United States Patent
Nord et al.

(10) Patent No.: US 11,654,299 B2
(45) Date of Patent: May 23, 2023

(54) METHODS AND APPARATUS PERTAINING TO RADIATION TREATMENT PLANS

(71) Applicant: Siemens Healthineers International AG, Steinhausen (CH)

(72) Inventors: Janne I. Nord, Espoo (FI); Hannu Laaksonen, Espoo (FI); Jan Schreier, Helsinki (FI); Jarkko Y. Peltola, Tuusula (FI); Christopher Boylan, Helsinki (FI)

(73) Assignee: Siemens Healthineers International AG, Steinhausen (CH)

( * ) Notice: Subject to any disclaimer, the term of this patent is extended or adjusted under 35 U.S.C. 154(b) by 256 days.

(21) Appl. No.: 16/919,746

(22) Filed: Jul. 2, 2020

(65) Prior Publication Data
US 2022/0001205 A1    Jan. 6, 2022

(51) Int. Cl.
*A61N 5/10*    (2006.01)
*G16H 20/40*   (2018.01)

(52) U.S. Cl.
CPC ............. *A61N 5/1031* (2013.01); *A61N 5/10* (2013.01); *A61N 5/103* (2013.01); *A61N 5/1042* (2013.01);
(Continued)

(58) Field of Classification Search
CPC ........ A61N 5/10; A61N 5/103; A61N 5/1031; A61N 2005/1041; A61N 5/1042;
(Continued)

(56) References Cited

U.S. PATENT DOCUMENTS

| 7,268,358 B2 * | 9/2007 | Ma .................... G21K 5/04 250/492.23 |
| 8,180,020 B2 * | 5/2012 | Kilby ................. A61N 5/10 378/65 |

(Continued)

OTHER PUBLICATIONS

Wilkens, Jan J. et al.; IMRT Treatment Planning Based on Prioritizing Prescription Goals; Physics in Medicine and Biology; Institute of Physics Publishing; Bristol, GB, vol. 52, No. 6; pp. 1675-1692; Mar. 21, 2007.
(Continued)

*Primary Examiner* — Allen C. Ho
(74) *Attorney, Agent, or Firm* — Fitch, Even, Tabin & Flannery LLP

(57) ABSTRACT

A control circuit accesses historical information regarding previously optimized radiation treatment plans for different patients and processes that information to determine the relative importance of different clinical goals. The circuit then facilitates development of a particular plan for a particular patient as a function of the relative importance of the clinical goals. By one approach the control circuit can be configured as a radiation treatment plan recommendation resource that accesses a database of radiation treatment plan formulation content items including at least one of a radiation treatment plan template, an auto-planning algorithm, and an auto-segmentation algorithm. By one approach the control circuit can be configured to, when presenting automatically-generated radiation treatment plans to a user, also co-present an opportunity for the user to signal to a remote entity that none of the plans are acceptable and that the user will instead employ a user-generated plan for the particular patient.

20 Claims, 3 Drawing Sheets

(52) U.S. Cl.
CPC ......... *A61N 5/1043* (2013.01); *A61N 5/1045* (2013.01); *A61N 5/1047* (2013.01); *A61N 5/1077* (2013.01); *A61N 5/1081* (2013.01); *G16H 20/40* (2018.01); *A61N 2005/1041* (2013.01)

(58) Field of Classification Search
CPC .. A61N 5/1043; A61N 5/1045; A61N 5/1047; A61N 5/1077; A61N 5/1081
USPC .......................................................... 378/65
See application file for complete search history.

(56) References Cited

U.S. PATENT DOCUMENTS

| | | | | |
|---|---|---|---|---|
| 9,192,782 | B1 * | 11/2015 | Grimm | A61N 5/1031 |
| 9,409,039 | B2 * | 8/2016 | Hartman | G16H 40/67 |
| 9,827,445 | B2 * | 11/2017 | Cordero Marcos | G16H 20/40 |
| 9,925,391 | B2 * | 3/2018 | Carpenter | G16H 10/60 |
| 10,046,177 | B2 * | 8/2018 | Sjölund | G06N 7/005 |
| 10,252,081 | B2 * | 4/2019 | Kauppinen | A61N 5/1042 |
| 10,475,537 | B2 * | 11/2019 | Purdie | G16H 50/20 |
| 10,489,556 | B2 * | 11/2019 | Nord | G16H 20/40 |
| 10,589,127 | B2 * | 3/2020 | Nord | A61N 5/103 |
| 10,653,893 | B2 * | 5/2020 | Kuusela | A61N 5/1031 |
| 10,661,096 | B2 * | 5/2020 | Kuusela | A61N 5/103 |
| 10,744,342 | B2 * | 8/2020 | Nord | G16H 50/50 |
| 10,762,167 | B2 * | 9/2020 | Hartman | A61N 5/103 |
| 10,792,514 | B2 * | 10/2020 | Ruokokoski | A61N 5/1036 |
| 10,850,120 | B2 * | 12/2020 | Laaksonen | A61N 5/1031 |
| 11,020,615 | B2 * | 6/2021 | Eriksson | A61N 5/1031 |
| 11,056,243 | B2 * | 7/2021 | Sjölund | A61N 5/103 |
| 11,167,150 | B2 * | 11/2021 | Löf | G16H 40/20 |
| 11,278,737 | B2 * | 3/2022 | Peltola | G06F 17/10 |
| 11,367,520 | B2 * | 6/2022 | Sjölund | G16H 50/20 |
| 2013/0085343 | A1 | 4/2013 | Toimela | |
| 2018/0178036 | A1 | 6/2018 | Laaksonen | |

OTHER PUBLICATIONS

Jee, Kyung-Wook et al.; Lexicographic Ordering: Intuitive Multicriteria Optimization for IMRT; Physics in Medicine and Biology; Institute of Physics Publishing; Bristol, GB; vol. 52, No. 7; pp. 1845-1861; Apr. 7, 2007.

International Search Report and Written Opinion from Application No. PCT/EP2021/067872, dated Sep. 21, 2021; 19 pages.

International Preliminary Report on Patentability from related Application No. PCT/EP2021/067872, dated Jan. 12, 2023; 12 pages.

* cited by examiner

METHODS AND APPARATUS PERTAINING TO RADIATION TREATMENT PLANS

TECHNICAL FIELD

These teachings relate generally to treating a patient's planning target volume with radiation pursuant to a radiation treatment plan and more particularly to generating a radiation treatment plan for that patient.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Obtaining optimal plans for a given patient can depend heavily on the planner's expertise and often requires several iterative interactions between the planner and the oncologist. To decrease both planning time and variation in treatment plan quality, some prior art approaches seek to automate at least a part of the planning process. Such approaches have improved the overall quality of the plans and ultimately led to better patient outcomes.

While that increasing use of automation to develop radiation treatment plans offers numerous advantages, the applicant has also determined that existing approaches in these regards do not necessarily meet all user needs in all application settings.

BRIEF DESCRIPTION OF THE DRAWINGS

The above needs are at least partially met through provision of the methods and apparatus pertaining to radiation treatment plans described in the following detailed description, particularly when studied in conjunction with the drawings, wherein.

Figure 1:
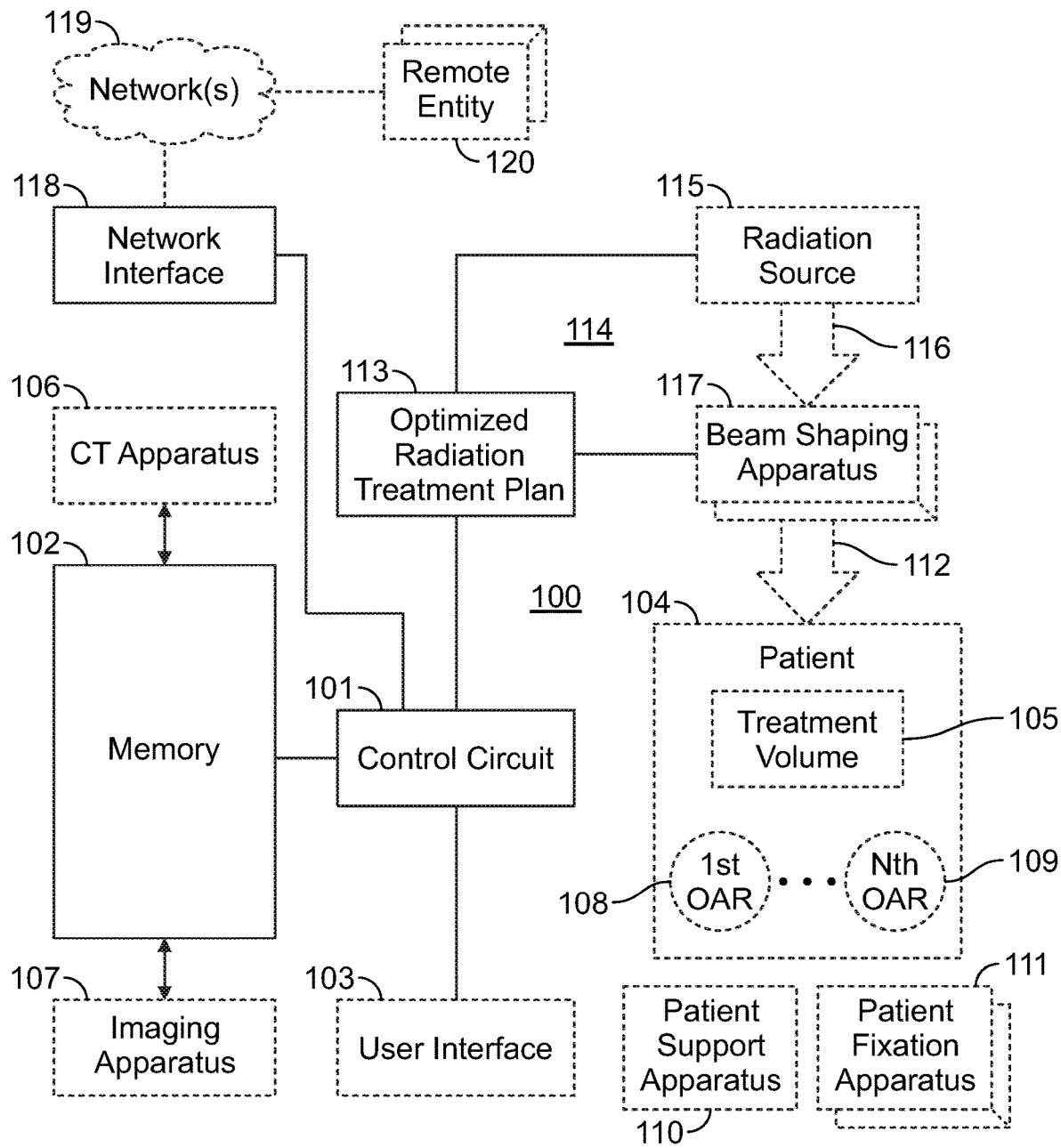
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments support the development of an optimized radiation treatment plan to effect radiation-based treatment of a patient's planning treatment volume. For the sake of an illustrative example these teachings can be carried out by an enabling control circuit.

By one approach the control circuit accesses historical information regarding a plurality of previously optimized radiation treatment plans corresponding to a plurality of different patients. The control circuit then processes that historical information to determine the relative importance of a plurality of different clinical goals. The control circuit can then facilitate development of a particular radiation treatment plan for a particular patient as a function, at least in part, of the foregoing relative importance of that plurality of clinical goals.

The aforementioned historical information can include, by way of example and at least in part, contemporaneous user-identified clinical goals and corresponding radiation dose information for at least some of the plurality of previously optimized radiation treatment plans.

Processing that historical information can include, by one approach, determining a relative importance of the plurality of clinical goals by automatically prioritizing the clinical goals with respect to relative importance. The latter automatic prioritization can be carried out as a function of contemporaneous user-identified clinical goals, acceptance of given ones of the plurality of previously optimized radiation treatment plans for usage in providing radiation treatment to a corresponding patient, and a frequency of usage of particular clinical goals within that historical information. By one approach, the aforementioned automatic prioritization of the clinical goals can comprise, at least in part, prioritizing frequently-used clinical goals higher than less-frequently used clinical goals.

By one approach the control circuit can be configured, at least in part, as a radiation treatment plan recommendation resource. In this case, and by one approach, the control circuit can access a database of radiation treatment plan formulation content items including at least one of a radiation treatment plan template, an auto-planning algorithm, and an auto-segmentation algorithm.

The control circuit can then recommend at least a particular one of these radiation treatment plan formulation content items to a user seeking to prepare a radiation treatment plan for a particular patient. That recommendation can comprise, by one approach and as one example, recommending a particular one of the radiation treatment plan templates as a function of at least one of user-based behavior and non-user-based behavior.

If desired, in lieu of the foregoing or in combination therewith, the control circuit can be configured to, when presenting a plurality of automatically-generated radiation treatment plans to a user as candidate radiation treatment plans for a particular patient, also co-present an opportunity for the user to signal to a remote entity both that none of the plurality of automatically-generated radiation treatment plans are acceptable and that the user will instead employ a user-generated radiation treatment plan for this particular patient.

By one approach the aforementioned opportunity can comprise a single user-assertable button. That "button" can be a physical button or, in a typical application setting, a virtual button. By one approach the aforementioned opportunity can further include an opportunity by which the user submits information regarding specifics of the user-generated radiation treatment plan to the remote entity.

By one approach the aforementioned remote entity is owned and/or operated on behalf of the entity that designed, distributes, operates, and or otherwise supports, in whole or in part, a platform that facilitates automatically generating radiation treatment plans. So configured, these teachings provide valuable feedback to that entity regarding whether that platform is providing useful deliverable content to the user base. That feedback can help guide refinement of the platform. When the feedback includes specifics regarding the user-generated radiation treatment plan that the user intends to use in lieu of any of the automatically generated plans, the specifics of the user-generated radiation treatment plan may be particularly valuable in refining and honing the operation of the platform.

These and other benefits may become clearer upon making a thorough review and study of the following detailed description. Referring now to the drawings, and in particular to FIG. 1, an illustrative apparatus 100 that is compatible with many of these teachings will now be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to optimization objectives information, patient geometry information, field geometry information, and so forth this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

In this illustrative example the control circuit 101 also operably couples to a network interface 118 that communicatively couples to one or more communication networks 119 (such as, but not limited to, the Internet). So configured the control circuit 101 can communicate with other elements (both within the apparatus 100 and external thereto, such as one or more remote entities 120) via the network interface 118. Network interfaces, including both wireless and non-wireless platforms, are well understood in the art and require no particular elaboration here.

By one approach, a computed tomography apparatus 106 and/or other non-CT imaging apparatus 107 as are known in the art can source some or all of any desired patient-related imaging information.

In this illustrative example the control circuit 101 is configured to ultimately output an optimized radiation treatment plan 113. This radiation treatment plan 113 typically comprises specified values for each of a variety of treatment-platform parameters during each of a plurality of sequential fields. In this case the radiation treatment plan 113 is generated through an optimization process. Various non-automated, automated, or partially-automated optimization processes specifically configured to generate such a radiation treatment plan are known in the art. As the present teachings are not overly sensitive to any particular selections in these regards, further elaboration in these regards is not provided here except where particularly relevant to the details of this description.

By one approach the control circuit 101 can operably couple to a radiation treatment platform 114 that is configured to deliver therapeutic radiation 112 to a corresponding patient 104 in accordance with the optimized radiation treatment plan 113. The patient 104 may have a treatment volume 105 and one or more organs-at-risk (OAR) as represented by a $1^{st}$ OAR through an Nth OAR (denoted by the reference numerals 108 and 109). These teachings are generally applicable for use with any of a wide variety of radiation treatment platforms. In a typical application setting the radiation treatment platform 114 will include a radiation source 115. The radiation source 115 can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical radiation treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more beam-shaping apparatuses 117 (such as jaws, multi-leaf collimators, and so forth) to provide selective beam shaping and/or beam modulation as desired. As the foregoing elements and systems are well understood in the art, further elaboration in these regards is not provided here except where otherwise relevant to the description.

Figure 2:
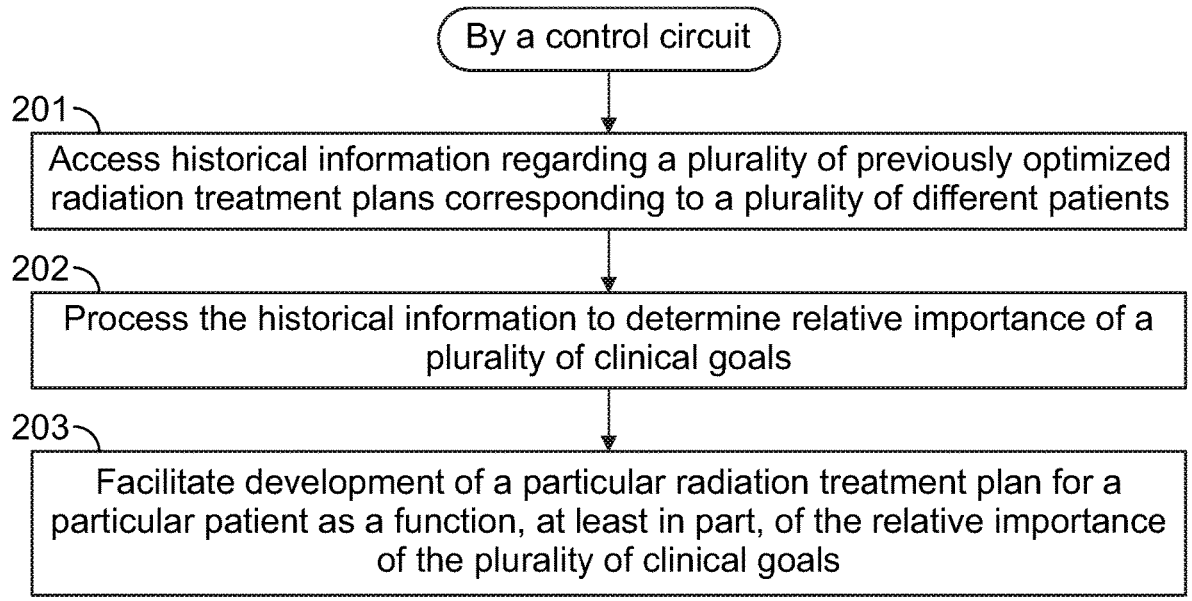
FIG. 2 comprises a flow diagram as configured in accordance with various embodiments of these teachings.

Referring now to FIG. 2, a process 200 that can be carried out, for example, by the above-described control circuit 101 will now be presented.

At block 201 the control circuit 101 accesses the aforementioned memory 102 (and/or a relevant remote entity or entities 120) to thereby access historical information regarding a plurality of previously optimized radiation treatment plans corresponding to a plurality of different patients. In this example the historical information includes, at least in part, contemporaneous user-identified clinical goals as well as corresponding radiation dose information for at least some (and perhaps all) of the plurality of previously optimized radiation treatment plans.

By one approach the aforementioned historical information pertains only to patients who received treatment at a particular treatment facility (such as a particular clinic). By another approach, in lieu of the foregoing or in combination therewith, the historical information only represents information for a circumscribed window of time, such as, for example, the most recent 5 years. By another approach the aforementioned historical information pertains to radiation treatment plans that were automatically planned using cloud resources. In this case plan information and/or corresponding metrics, parameters, or other metadata for radiation treatment plans for a variety of treatment facilities and a variety of users can be collected and aggregated for these purposes.

Generally speaking, this historical information directly or indirectly represents such things as extracted clinical goals and dose information (represented, for example, as dose volume histograms) for the indicated radiation treatment plans. In particular, the corresponding system can collect user-provided clinical goals that are used for automatic planning purposes along with the resulting dose volume histogram curves into a corresponding database.

In a typical application setting, the information can be anonymized and therefore not correlated to any particular patient when accessed as described.

By one approach, the radiation treatment plans in the historical information can be clustered according to treatment type and/or site. Using this approach, the control circuit 101 may only access historical information pertaining to a treatment type and/or treatment site that is identical to or at least sufficiently similar (as determined by the user and/or the system) to a current patient's individual needs and or requirements.

At block 202, the control circuit 101 processes the aforementioned historical information to determine the relative importance of a plurality of clinical goals. This activity can include automatically prioritizing those clinical goals with respect to relative importance. By one approach the latter can be undertaken as a function of one or more of: contemporaneous user-identified clinical goals, acceptance of given ones of the plurality of previously optimized radiation treatment plans for usage in providing radiation treatment to a corresponding patient, and/or frequency of usage of particular clinical goals within the historical information. (As regards the latter, and generally speaking, these teachings will accommodate prioritizing frequently-used clinical goals higher than less-frequently used clinical goals.)

By one approach, these teachings will accommodate calculating a pass/fail rate for each and all clinical goals in the aforementioned database based on the aforementioned dose volume histogram curves in that database.

More particularly, these teachings will facilitate rating plan quality based on the historical information, at least in part, by employing a pass/fail ratio that indicates the relative importance of meeting a particular clinical goal. For example, a clinical goal that is never met in any of the plans in the historical information would be rated as being less important than clinical goals that are met in all of the plans.

As one illustrative example in these regards, and without intending to suggest any limitations with respect to these teachings, a plan quality index (PQ) can be defined as follows:

$$PQ=(\Sigma w\_i * c\_i)/(\Sigma w\_i)$$

where $w\_i$ is a weight parameter provided by the pass rate in the historical information and $c\_i$ is the pass rate that corresponds to a current plan under consideration.

In such a case, the pass rate would be "1" when the clinical goal is met. The shape of the function can be selected as required. One possible implementation employs a step function (where the pass value is "0" if the goal is not met) while another possible implementation employs a distance metric from a defined optimal value for the metric. One way to derive an optimal metric would be to find from the historical information a value after which the pass rate of the clinical goals drops below a set threshold. For example, one could define as the optimal level a value that is met in at least 50 percent of the existing plans being considered.

Those skilled in the art will appreciate that more complex weighting functions can be employed for $c\_i$ aside from a step function. In that case it becomes readily possible to differentiate even plans where all clinical goals are met.

By one approach, a relative plan quality rank (PQR) index could be derived by weighting the plan quality index with the ratio of plans that have a lower plan quality index in the historical information. This approach can set the plan quality index in relative terms to the historically achieved plan quality index for a particular treatment clinic or more globally as desired. In such a case, a plan quality rank index of 50 percent would represent an average plan, where half of the plans performed better and half performed worse.

Table 1 presents an illustrative example in these regards. In this example the control circuit 101 employs a step function for defining c_i. For a plan that would meet clinical goals for the planning treatment volume and a first organ-at-risk ("spine") but not a second organ-at-risk ("lens"), the plan quality index PQ could be calculated as follows:

$$PQ = \frac{1*1 + 0.9*1 + 0.1*0}{1 + 0.9 + 1} = \frac{1.9}{2}$$

Upon querying the historical information the control circuit 101 can find that the ratio of plans where the plan quality index is lower than 1.9/2 is 70 percent. Therefore, the resulting PQR is 70 percent.

TABLE 1

Structure clinical goal pass rate
Planning treatment volume 100% volume receives 99% of the prescribed dose of 100%
Spine 0% volume receives at most 35 Gy 90%
Lens 0% receives at most 5 Gy 10%

Those skilled in the art will appreciate that, over time, clinical goals would not be needed to estimate plan quality as quality could be estimated from the aforementioned historical information. This historical information could also be used to provide a useful set of clinical goals best suited for a given treatment type.

These teachings are highly practical in use and will accommodate various modifications, additions, and/or application settings. For example, these teachings can be applied to facilitate comparing one plan to another, to improve the planning process for radiation treatment plans, to find clinical goals that are most useful (i.e., that are the most used and also that have a high pass rate) to facilitate quality assurance, and so forth.

As further examples, these teachings can be modified to facilitate filtering plans (to reveal, for example, that 5% of plans in the historical information reach a particular level of plan quality), to facilitate clustering plans by diagnosis, user classification, treatment protocol, or other criterion of choice (to thereby facilitate, for example, comparing different clinical sites to one another according to their plan quality metrics), to determine the most useful other clinical goals in the database by, for example, clustering plans according to similarity in use, or to provide a set of refined goals based on user-given clinical goals (for example, if the user has specified clinical goals for a target structure in the head and neck region of a patient and for the left parotid as organs-at-risk, the system could provide additional goals for the structures but not for the right parotid because it was excluded by the user when initially setting the clinical goals).

At block 203, the control circuit 101 facilitates development of a particular radiation treatment plan for a particular patient as a function, at least in part, of the aforementioned relative importance of the plurality of clinical goals. This activity may, if desired, include presenting some or all of the aforementioned information on a display that comprises a part of the aforementioned user interface 103. These teachings will then of course accommodate using the developed radiation treatment plan for this particular patient using the corresponding radiation treatment platform 114.

By one approach, in lieu of the foregoing or in combination therewith, these teachings will accommodate automatically proposing the use of recommended resources to facilitate formulating radiation treatment plans that then reflect, directly or indirectly, content that has been used for similar patients and indications (both within the user's organization and globally). Such an approach can help ameliorate the problem of finding appropriate plan strategies for particular patients when traditional approaches in those regards may be difficult and highly subjective. Such an approach can also help avoid user tendencies to habitually create similar plans for different patients at a given treatment site and/or for different patient presentations.

Figure 3:
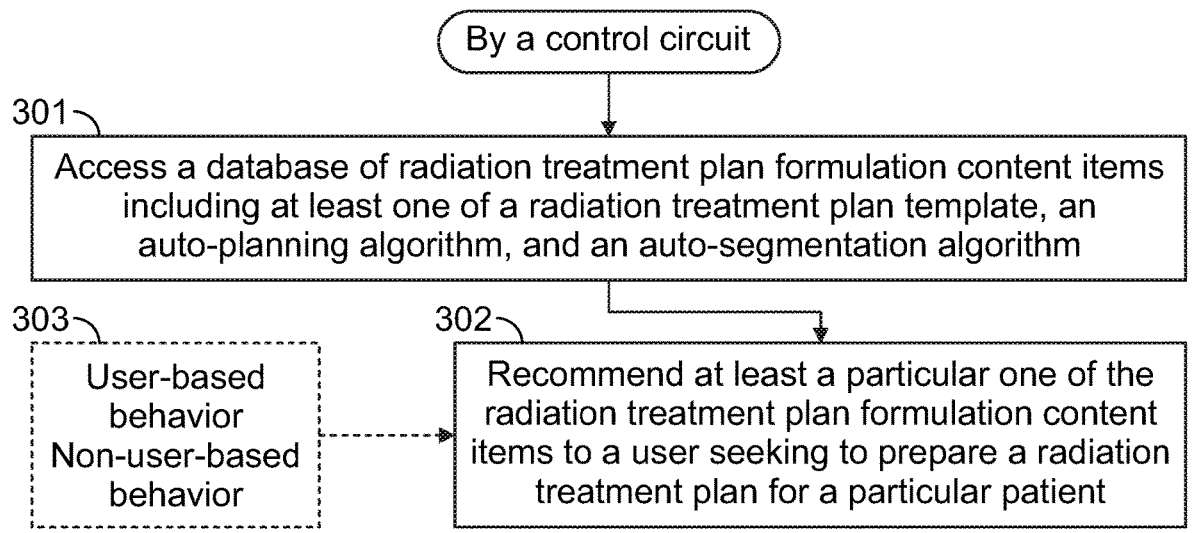
FIG. 3 comprises a flow diagram as configured in accordance with various embodiments of these teachings.

Referring now to FIG. 3, pursuant to this process 300 the control circuit 101 (at block 301) accesses a database of radiation treatment plan formulation content items. In this illustrative example, these items are not previously optimized radiation treatment plans in and of themselves. Instead, these items comprise content suitable and sufficient to facilitate formulating an optimized radiation treatment plan. These teachings will accommodate various kinds of items including, but not limited to, radiation treatment plan templates, auto-planning algorithms (including, for example, intensity-modulated radiation therapy (IMRT) auto-planning algorithms and volumetric modulated arc therapy (VMAT) auto-planning algorithms), and auto-segmentation algorithms. Such items are known in the art and require no further elaboration here. Accordingly, this activity can comprise accessing at least one or more of the aforementioned radiation treatment plan formulation content items.

By one approach, the aforementioned radiation treatment plan templates can include templates that are commonly used and hence can be recommended based on a user's previous planning patterns. These teachings will also accommodate employing an exploratory component to thereby purposefully recommend planning techniques that may, for example, be trending positively in the larger medical community or at the treatment facility for this particular user.

This database may reside, in whole or in part, in the aforementioned memory 102. By another approach, in lieu of the foregoing or in combination therewith, at least some of the accessed content may reside with a remote entity 120. The latter may be particularly applicable in application settings where cloud-based services offered by the remote entity 120 are employed to develop radiation treatment plans. In such a case, the building of a data-driven recommendation system can be based at least in part upon aggregated information derived from such activity.

At block 302, the control circuit 101 then recommends at least a particular one of the aforementioned radiation treatment plan formulation content items to a user seeking to prepare a radiation treatment plan for a particular patient. By one approach, this recommendation can be offered as a function of one or more behaviors 303. For example, the recommendation can be based upon at least one of user-based behavior and non-user-based behavior.

The foregoing activity can include, for example, analyzing user patterns pertaining to formulating previous radiation treatment plans. This can include, for example, taking into account which type of plans tend to be employed at which treatment sites, for what kinds of overall patient anatomy, and/or for what kind, relative position, size, and/or shape of tumor.

By one approach, when the accessed radiation treatment plan formulation content item comprises an auto-segmentation algorithm, the recommendation can serve to suggest particular patient structures that are typically contoured for similar cases. Again, such a recommendation may be based on either typical local practices (either for this particular user or for the user's application setting which may account for other local users as well) and/or broader, global practices.

If desired, the foregoing recommendation activity can be based on heuristic algorithms such as a fixed, non-evolving list of plans that are suggested based on one or more hardcoded similarity metrics.

So configured, plan/treatment quality can be improved, both by assuring reuse of previous best practices and also by selectively exposing the user to best practices that may be beyond the scope of their present experience and even the experience of their present treatment facility.

Those skilled in the art will know that non-automated treatment planning involves manually doing such things as establishing the treatment machine isocenter and field configuration, drawing important structures into the patient images by hand, setting up optimization objectives for the treatment plan optimizer, and manually fine-tuning the latter until the desired dosing is achieved. Accordingly, problems experienced by the user tend to be quite specific and intuitively associated with certain corresponding manual actions. As automated planning becomes more mainstream, however, the latter intuitive understanding is diminished. The main input for the user becomes a list of clinical goals that can be difficult to fine tune on the fly. In some cases the user is simply left with selecting a suitable plan from a selection of treatment plans generated by the automated process. When none of those plans meets the user's expectations, the user instead typically reverts to creating a plan manually that the user then utilizes when treating the patient.

The applicant has determined that the foregoing scenario does nothing to facilitate improvement of the automated planning process. In particular, the entity that designs and/or otherwise supports the automated planning process has no information to inform improvements based upon such scenarios.

Figure 4:
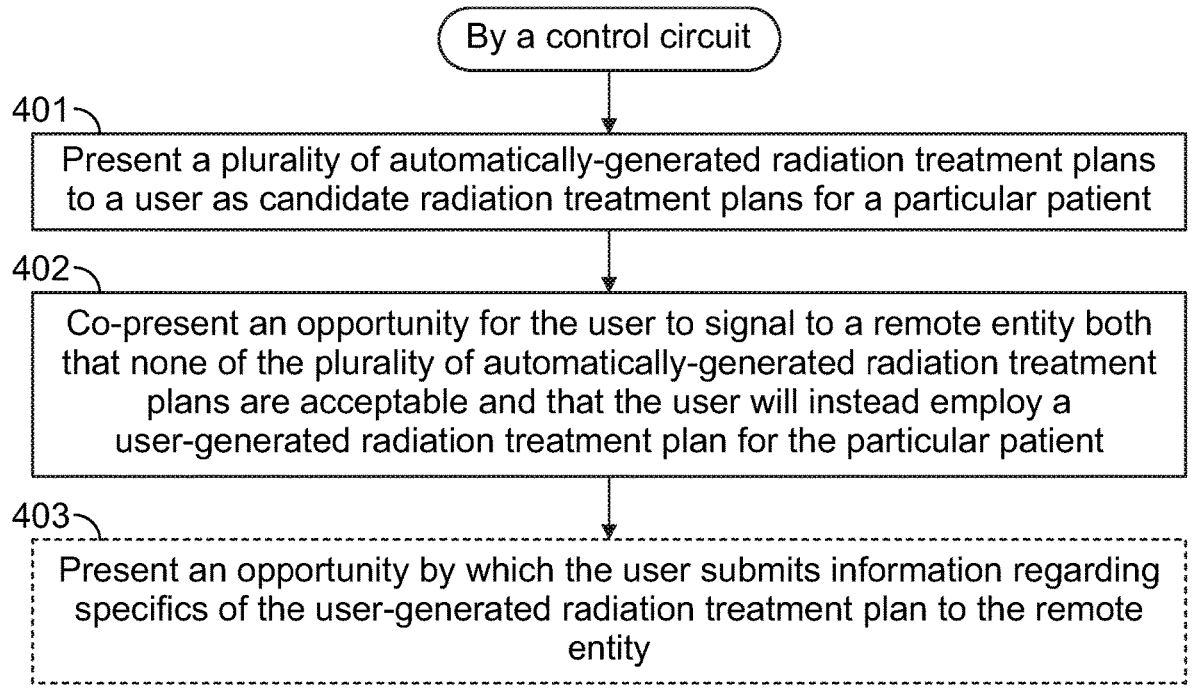
FIG. 4 comprises a flow diagram as configured in accordance with various embodiments of these teachings.

With the foregoing in mind, and referring now to FIG. 4, a process 400 will be described that can be employed in lieu of the previously described processes or in combination therewith.

At block 401, the control circuit 101 presents (for example, via a display that comprises a part of the aforementioned user interface 103) a plurality of automatically-generated radiation treatment plans to a user as candidate radiation treatment plans for a particular patient. These teachings will accommodate a variety of different ways of automatically generating these plans.

At block 402, and while also presenting the aforementioned plurality of automatically-generated radiation treatment plans, the control circuit 101 simultaneously co-presents an opportunity for the user to signal to a remote entity 120 (such as the entity that designs, distributes, and or supports the relevant service that facilitates automatically-generating this plurality of plans) both that none of the plurality of automatically-generated radiation treatment plans are acceptable and that the user will instead employ a user-generated radiation treatment plan for the particular patient.

Figure 5:
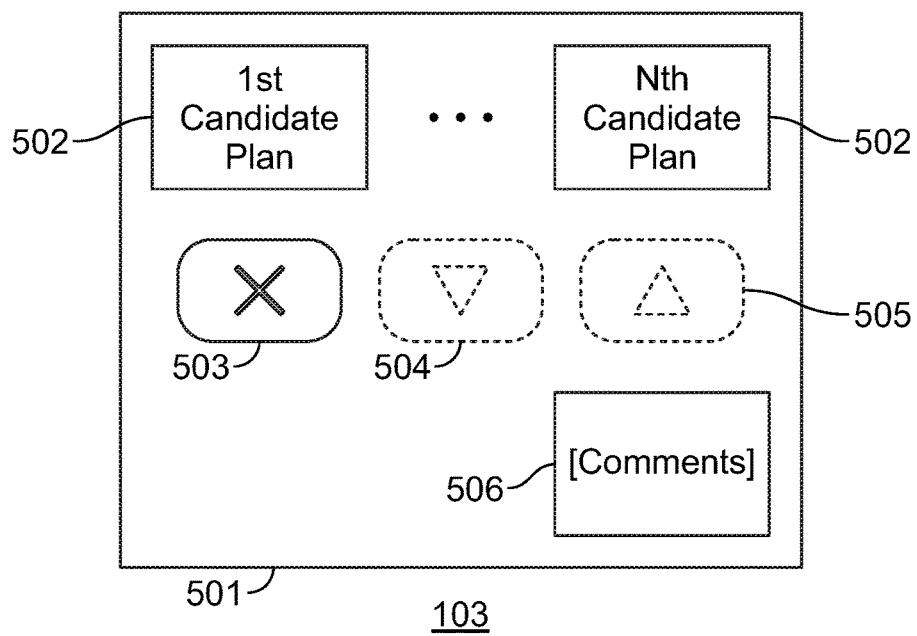
FIG. 5 comprises a schematic screen shot as configured in accordance with various embodiments of these teachings.

FIG. 5 presents one illustrative example in these regards. In this example a display 501 that comprises a part of the user interface 103 presents the plurality of automatically-generated radiation treatment plans 502 along with a single user-assertable virtual button 503. By one approach the display 501 also presents a user-assertable button 504 by which the user can upload or transfer to the current platform the user-generated radiation treatment plan that they intend to select for use with this particular patient. So configured, and by one approach, in response to asserting the aforementioned button 503 the control circuit 101 will signal a corresponding remote entity 120 that none of the plurality of automatically-generated radiation treatment plans 502 are acceptable and that the user will instead employ a user-generated radiation treatment plan for the particular patient.

By one approach, asserting the aforementioned button 503 will also cause automatic transmission of either the complete user-generated radiation treatment plan or an abridged version thereof to the same corresponding remote entity 120. By another approach, if desired, and as shown at optional block 403 of FIG. 4, these teachings will provide for providing an opportunity by which the user submits information regarding specifics of the user-generated radiation treatment plan to a remote entity. In particular, and referring again to FIG. 5, asserting the aforementioned button 503 can cause the control circuit 101 to provide an opportunity via another button 505 to upload either the complete user-generated radiation treatment plan or a abridged version thereof to the remote entity 120.

In lieu thereof or in combination therewith, the control circuit 101 can present an opportunity 506 for the user to include other relevant information regarding, for example, why they find the automatically-generated plans to be unacceptable. This opportunity 506 may comprise, for example, a free text field and/or a number of selectable standard responses by which the user can quickly identify the reason (s) for their current selection. Using this approach, the system can query the user to determine, for example, the critical feature that the user expected and that was absent from the automatically-generated plans or some other reason why the automatically-generated plans cannot be used in treatment for this patient.

Such an approach allows the user to easily, intuitively, and quickly report the perceived failure of the automated system and also offers an opportunity for the user to provide additional information that the remote entity 120 can utilize to identify improvements that can be made to the automated system.

In a typical application setting the automated system will generate the candidate plans by sometimes automatically trying to mimic a typical user, in which case the process is driven at least in part by corresponding clinical goals along with additional goals for dose features that may be based upon, for example, input gleaned from clinical experts. In many cases a main reason for an automatically-generated plan to fail clinical expectations is that the process has not suitably accounted for certain dose aspects. In such a case the process may be expected to yield similar results until the decision assumptions are corrected.

Configured as described above, however, the described single-button interface permits a user to report unsatisfactory results while also allowing the user to provide details regarding a satisfactory plan, written feedback, or other helpful information that can serve to hone and improve the automated process both for this user and others. Useful information that can be gleaned from any of the foregoing may include, for example, dose volume histograms or other dose information.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method comprising:
by a control circuit:
accessing historical information regarding a plurality of previously optimized radiation treatment plans corresponding to a plurality of different patients;
processing the historical information to determine a relative importance of a plurality of clinical goals; and
facilitating a development of a particular radiation treatment plan for a particular patient as a function, at least in part, of the relative importance of the plurality of clinical goals.

2. The method of claim 1, wherein the historical information includes, at least in part, contemporaneous user-identified clinical goals and corresponding radiation dose information for at least some of the plurality of previously optimized radiation treatment plans.

3. The method of claim 1, wherein processing the historical information to determine a relative importance of a plurality of clinical goals includes automatically prioritizing the plurality of clinical goals with respect to the relative importance.

4. The method of claim 3, wherein automatically prioritizing the plurality of clinical goals with respect to the relative importance includes prioritizing the plurality of clinical goals as a function of:
contemporaneous user-identified clinical goals;
an acceptance of given ones of the plurality of previously optimized radiation treatment plans for a usage in providing a radiation treatment to a corresponding patient; and
a frequency of usage of particular clinical goals within the historical information.

5. The method of claim 3, wherein automatically prioritizing the plurality of clinical goals with respect to the relative importance includes prioritizing frequently-used clinical goals higher than less-frequently used clinical goals.

6. The method of claim 1, wherein the control circuit is further configured as a radiation treatment plan recommendation resource, and wherein the method further comprises, by the control circuit, accessing a database of radiation treatment plan formulation content items including at least one of a radiation treatment plan template, an auto-planning algorithm, and an auto-segmentation algorithm, and recommending at least a particular one of the radiation treatment plan formulation content items to a user seeking to prepare a radiation treatment plan for a particular patient.

7. The method of claim 6, wherein recommending at least a particular one of the radiation treatment plan formulation content items comprises recommending the at least a particular one of the radiation treatment plan formulation content items as a function of at least one of:
a user-based behavior; and
a non-user-based behavior.

8. The method of claim 1, wherein the control circuit is further configured to, when presenting a plurality of automatically-generated radiation treatment plans to a user as candidate radiation treatment plans for a particular patient, also co-present an opportunity for the user to signal to a remote entity both that none of the plurality of automatically-generated radiation treatment plans are acceptable and that the user will instead employ a user-generated radiation treatment plan for the particular patient.

9. The method of claim 8, wherein the opportunity comprises a single user-assertable button.

10. The method of claim 8, wherein the opportunity further includes an opportunity by which the user submits information regarding specifics of the user-generated radiation treatment plan to the remote entity.

11. An apparatus comprising:
a control circuit configured to:
access historical information regarding a plurality of previously optimized radiation treatment plans corresponding to a plurality of different patients;
process the historical information to determine a relative importance of a plurality of clinical goals; and
facilitate a development of a particular radiation treatment plan for a particular patient as a function, at least in part, of the relative importance of the plurality of clinical goals.

12. The apparatus of claim 11, wherein the historical information includes, at least in part, contemporaneous user-identified clinical goals and corresponding radiation dose information for at least some of the plurality of previously optimized radiation treatment plans.

13. The apparatus of claim 11, wherein the control circuit is configured to process the historical information to determine a relative importance of a plurality of clinical goals by, at least in part, automatically prioritizing the plurality of clinical goals with respect to the relative importance.

14. The apparatus of claim 13, wherein the control circuit is configured to automatically prioritize the plurality of clinical goals with respect to the relative importance by, at least in part, prioritizing the plurality of clinical goals as a function of:
contemporaneous user-identified clinical goals;
an acceptance of given ones of the plurality of previously optimized radiation treatment plans for a usage in providing a radiation treatment to a corresponding patient; and
a frequency of usage of particular clinical goals within the historical information.

15. The apparatus of claim 13, wherein the control circuit is configured to automatically prioritize the plurality of clinical goals with respect to the relative importance by, at least in part, prioritizing frequently-used clinical goals higher than less-frequently used clinical goals.

16. The apparatus of claim 11, wherein the control circuit is further configured as a radiation treatment plan recommendation resource that accesses a database of radiation treatment plan formulation content items including at least one of a radiation treatment plan template, an auto-planning algorithm, and an auto-segmentation algorithm, and recommends at least a particular one of the radiation treatment plan formulation content items to a user seeking to prepare a radiation treatment plan for a particular patient.

17. The apparatus of claim 16, wherein the control circuit is further configured to recommend at least a particular one of the radiation treatment plan formulation content items by recommending the at least a particular one of the radiation treatment plan formulation content items as a function of at least one of:
a user-based behavior; and
a non-user-based behavior.

18. The apparatus of claim 11, wherein the control circuit is further configured to, when presenting a plurality of automatically-generated radiation treatment plans to a user as candidate radiation treatment plans for a particular patient, also co-present an opportunity for the user to signal to a remote entity both that none of the plurality of automatically-generated radiation treatment plans are acceptable and that the user will instead employ a user-generated radiation treatment plan for the particular patient.

19. The apparatus of claim 18, wherein the opportunity comprises a single user-assertable button.

20. The apparatus of claim 18, wherein the opportunity further includes an opportunity by which the user submits information regarding specifics of the user-generated radiation treatment plan to the remote entity.

* * * * *